United States Patent
Ingwer et al.

(10) Patent No.: US 11,633,283 B2
(45) Date of Patent: *Apr. 25, 2023

(54) COMPONENTS FOR ARTIFICIAL JOINTS

(71) Applicant: ARTHREX, INC., Naples, FL (US)

(72) Inventors: Zachary Ingwer, Boca Raton, FL (US); Scott Sherman, Naples, FL (US); Joel Zubizarreta, Naples, FL (US)

(73) Assignee: ARTHREX, INC., Naples, FL (US)

(*) Notice: Subject to any disclaimer, the term of this patent is extended or adjusted under 35 U.S.C. 154(b) by 391 days.

This patent is subject to a terminal disclaimer.

(21) Appl. No.: 16/684,818

(22) Filed: Nov. 15, 2019

(65) Prior Publication Data

US 2020/0078177 A1 Mar. 12, 2020

Related U.S. Application Data

(63) Continuation of application No. 15/908,862, filed on Mar. 1, 2018, now Pat. No. 10,512,543, which is a (Continued)

(51) Int. Cl.
*A61F 2/38* (2006.01)
*A61F 2/28* (2006.01)
*A61F 2/30* (2006.01)

(52) U.S. Cl.
CPC ........ *A61F 2/2846* (2013.01); *A61F 2/30749* (2013.01); *A61F 2/38* (2013.01); *A61F 2/389* (2013.01); *A61F 2/3859* (2013.01); *A61F 2/30767* (2013.01); *A61F 2002/285* (2013.01); *A61F 2002/3085* (2013.01); *A61F 2002/3093* (2013.01); *A61F 2002/30332* (2013.01); *A61F 2002/30354* (2013.01); *A61F 2002/30535* (2013.01); *A61F 2002/30579* (2013.01); (Continued)

(58) Field of Classification Search
CPC ....................... A61F 2/3859; A61F 2002/2835
See application file for complete search history.

(56) References Cited

U.S. PATENT DOCUMENTS

| 4,865,607 A | 9/1989 | Witzel et al. |
| 4,938,769 A | 7/1990 | Shaw |

(Continued)

FOREIGN PATENT DOCUMENTS

| CN | 101708138 A | 5/2010 |
| WO | 2015090834 A1 | 6/2015 |

OTHER PUBLICATIONS

International Search Report and Written Opinion for International Application No. PCT/US2017/031979, dated Jul. 31, 2017.

(Continued)

*Primary Examiner* — Jason-Dennis N Stewart
(74) *Attorney, Agent, or Firm* — Carlson, Gaskey & Olds, P.C.

(57) ABSTRACT

A component of an artificial joint according to an exemplary aspect of the present disclosure includes, inter alia, a hollow tube including bone ingrowth material. Further, the hollow tube is selectively expandable. The bone ingrowth material allows the component to become biologically fixed to adjacent bone. Further, expansion of the hollow tube increases friction between the hollow tube and the adjacent bone, which increases stability.

14 Claims, 5 Drawing Sheets

Related U.S. Application Data continuation of application No. 15/185,755, filed on Jun. 17, 2016, now Pat. No. 9,907,655.

(52) U.S. Cl.
CPC .............. *A61F 2002/30624* (2013.01); *A61F 2002/30878* (2013.01); *A61F 2002/3895* (2013.01)

(56) References Cited

U.S. PATENT DOCUMENTS

| | | | |
|---|---|---|---|
| 5,062,852 A | 11/1991 | Dorr et al. | |
| 5,282,861 A | 2/1994 | Kaplan | |
| 5,326,359 A | 7/1994 | Oudard | |
| 5,556,433 A | 9/1996 | Gabriel et al. | |
| 5,658,341 A | 8/1997 | Delfosse | |
| 6,319,255 B1 | 11/2001 | Grundei et al. | |
| 7,578,850 B2 | 8/2009 | Kuczynski et al. | |
| 7,615,080 B2 | 11/2009 | Ondrla | |
| 8,192,497 B2 | 6/2012 | Ondrla | |
| 8,241,367 B2 | 8/2012 | Justin et al. | |
| 2002/0049501 A1 | 4/2002 | Storer et al. | |
| 2003/0233149 A1 | 12/2003 | Hodorek | |
| 2004/0039447 A1 | 2/2004 | Simon et al. | |
| 2004/0138748 A1 | 7/2004 | Boyer, II et al. | |
| 2004/0172138 A1 | 9/2004 | May et al. | |
| 2009/0270994 A1 | 10/2009 | Schaefer et al. | |
| 2010/0094292 A1* | 4/2010 | Parrott .............. | A61B 17/7283 606/62 |

OTHER PUBLICATIONS

International Preliminary Report on Patentability for International Application No. PCT/US2017/031979, dated Dec. 18, 2018.

* cited by examiner

COMPONENTS FOR ARTIFICIAL JOINTS

RELATED APPLICATIONS

This application is a continuation of U.S. application Ser. No. 15/908,862, filed Mar. 1, 2018, which is a continuation of U.S. application Ser. No. 15/185,755, filed Jun. 17, 2016 (now issued as U.S. Pat. No. 9,907,655), the entire disclosures of which are hereby incorporated by reference.

BACKGROUND

This disclosure relates to components for artificial joints and, more particularly, to artificial femoral and tibial components for use during unicondylar or total knee arthroplasty procedures.

A total knee arthroplasty, also known as total knee replacement, is a surgical procedure in which parts of the knee joint are replaced with artificial components (sometimes referred to as prostheses). In a typical total knee arthroplasty procedure, an artificial femoral component is attached to the femur, an artificial tibial component is attached to the tibia, and a spacer is provided between the femoral and tibial components.

SUMMARY

This disclosure describes components for artificial joints. The components can be used during joint replacement procedures. For example, the components could be artificial femoral or tibial components for use during unicondylar or total knee arthroplasty procedures.

An artificial joint component according to an exemplary aspect of the present disclosure includes, inter alia, a hollow tube including bone ingrowth material. Further, the hollow tube is selectively expandable. The bone ingrowth material allows the component to become biologically fixed to adjacent bone. Further, expansion of the hollow tube increases friction between the hollow tube and the adjacent bone, which increases stability.

In a further embodiment, the component includes an opening aligned with the hollow tube, and a plug receivable in the opening. The plug is configured to engage an interior of the hollow tube to expand the hollow tube. The hollow tube may, in some embodiments, include a slit along substantially the entire length thereof to allow for expansion.

An artificial knee according to an exemplary aspect of the present disclosure includes, inter alia, an artificial femoral component including a hollow tube having bone ingrowth material, and an artificial tibial component including a hollow tube having bone ingrowth material. Further, the hollow tube of one of the artificial femoral component and the artificial tibial component is selectively expandable. Additionally, the artificial knee includes a spacer located between the artificial femoral component and the artificial tibial component.

In a further embodiment, the artificial femoral component further includes an anterior surface providing an articulating surface relative to the spacer. The artificial femoral component also includes a posterior surface substantially covered by bone ingrowth material. Further, the hollow tube of the artificial femoral component projects in a posterior direction from the posterior surface.

A method according to an exemplary aspect of the present disclosure includes, inter alia, expanding a hollow tube of a component of an artificial joint, the hollow tube including bone ingrowth material.

DETAILED DESCRIPTION

This disclosure describes components for artificial joints. The components can be used during joint replacement procedures. For example, the components could be artificial femoral or tibial components for use during unicondylar or total knee arthroplasty procedures.

In some embodiments, a component of an artificial joint includes a hollow tube having bone ingrowth material. The hollow tube includes bone ingrowth material adapted to provide stability to the component via biological fixation. The hollow tube is also selectively expandable. Expansion of the hollow tube increases friction between the hollow tube and the adjacent bone, which further increases fixation. The artificial components of the present disclosure are "cementless," i.e., they can be fixed to bone without the use of bone cement.

In a further embodiment, the component includes an opening aligned with the hollow tube, and a plug receivable in the opening. The plug is configured to engage an interior of the hollow tube to expand the hollow tube.

In a further embodiment, the opening and the plug are threaded.

In a further embodiment, the plug includes a threaded shank projecting beyond the hollow tube and configured to engage bone.

In a further embodiment, the plug includes a flared portion distal of the threads, the flared portion configured to engage an interior of the hollow tube.

In a further embodiment, the hollow tube includes at least one slit along a substantially an entire length thereof.

In a further embodiment, the hollow tube includes a layer of bone ingrowth material provided on a substantially solid backing material.

In a further embodiment, the hollow tube consists of bone ingrowth material.

In a further embodiment, the hollow tube is substantially cylindrical and defines an interior cavity.

In a further embodiment, the component is a tibial tray, and wherein the hollow tube projects from an inferior surface of the tibial tray.

An artificial knee according to an exemplary aspect of the present disclosure includes, inter alia, an artificial femoral component including a hollow tube having bone ingrowth material, and an artificial tibial component including a hollow tube having bone ingrowth material. Further, the hollow tube of one of the artificial femoral component and the artificial tibial component is selectively expandable. Additionally, the artificial knee includes a spacer located between the artificial femoral component and the artificial tibial component.

In a further embodiment, the artificial femoral component further includes an anterior surface comprising an articulating surface relative to the spacer. The artificial femoral component also includes a posterior surface substantially covered by bone ingrowth material. Further, the hollow tube of the artificial femoral component projects in a posterior direction from the posterior surface.

In a further embodiment, the artificial femoral component includes two hollow tubes, and each of the hollow tubes of the artificial femoral component includes bone ingrowth material.

In a further embodiment, the artificial tibial component further includes an opening aligned with the hollow tube of the artificial tibial component, and a plug receivable in the opening. The plug is configured to engage an interior of the hollow tube to expand the hollow tube.

In a further embodiment, the opening and the plug are threaded.

In a further embodiment, the plug includes one of (1) a threaded shank projecting beyond the hollow tube and configured to engage bone, and (2) a flared portion distal of the threads and configured to engage the hollow tube.

In a further embodiment, the hollow tube of the artificial tibial component includes at least one slit along substantially the entire length thereof.

A method according to an exemplary aspect of the present disclosure includes, inter alia, expanding a hollow tube of a component of an artificial joint, the hollow tube including bone ingrowth material.

In a further embodiment, the method further includes forming a hole in bone and inserting the hollow tube into the hole. The hollow tube is sized to substantially correspond to the size of the hole.

In a further embodiment, the hollow tube is expanded as a plug is inserted into an opening of the component.

Figure 1:
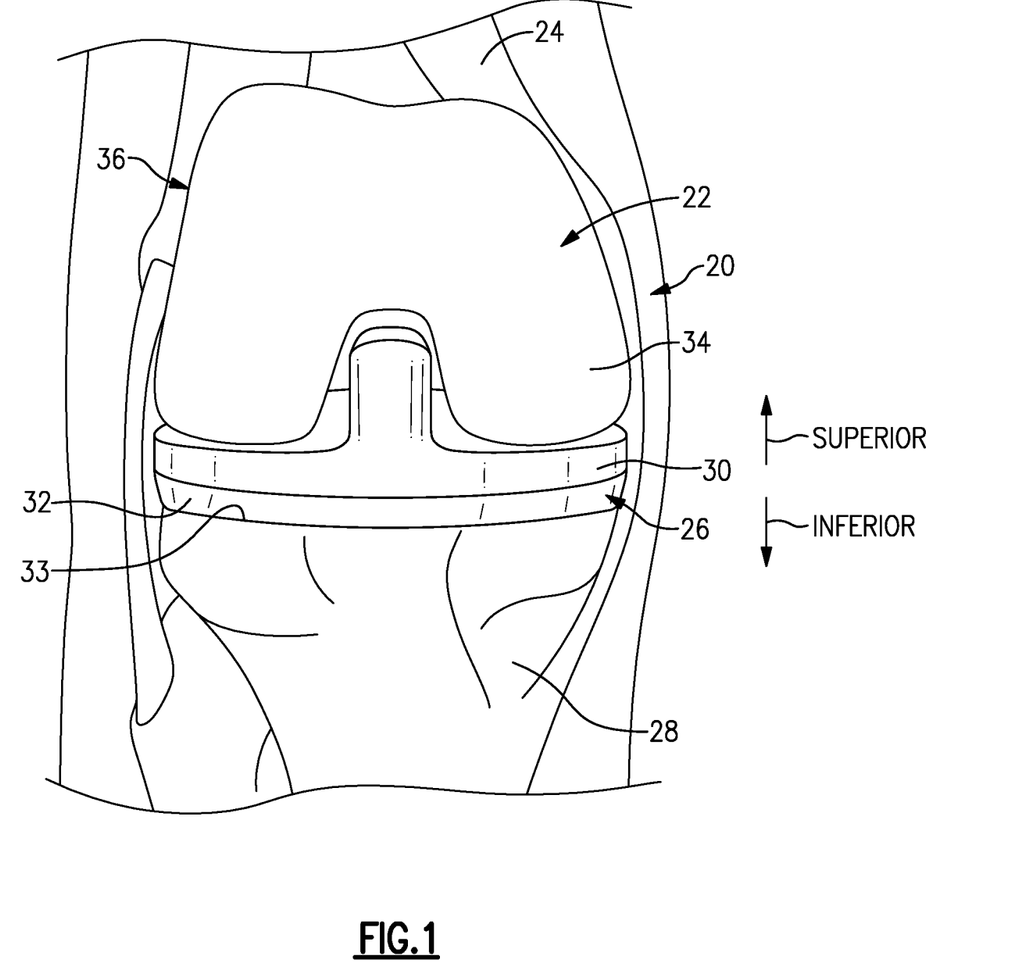
FIG. 1 illustrates an example artificial joint. In this example, the artificial joint is an artificial knee.

FIG. 1 illustrates an example artificial joint 20. In this non-limiting example, the artificial joint 20 is an artificial knee. While an artificial knee is specifically mentioned herein, this disclosure is not limited to artificial knees and can have applications in other parts of the body.

The artificial joint 20 includes an artificial femoral component 22 connected to a femur 24, an artificial tibial component 26 connected to a tibia 28, and a spacer 30 arranged between the artificial femoral component 22 and the artificial tibial component 26. In this non-limiting example, the artificial femoral and tibial components 22, 26 are made of metallic materials, and the spacer 30 is made of a plastic material. However, this disclosure is not limited to these particular materials.

In a non-limiting example, the artificial tibial component 26 is a tibial tray having a base plate 32. A superior, or top, portion of the base plate 32 is configured to support the spacer 30, and the inferior, or bottom, of the base plate 32 is configured to mate with a tibial plateau cut 33. The "superior" and "inferior" directions are labeled in the figures for purposes of explanation only.

The artificial femoral component 22 includes an anterior surface 34, which provides an articulating surface that engages the spacer 30. The artificial femoral component 22 further includes a posterior surface 36 configured to mate with cuts of the femur 24.

Figures 2A, 2B:
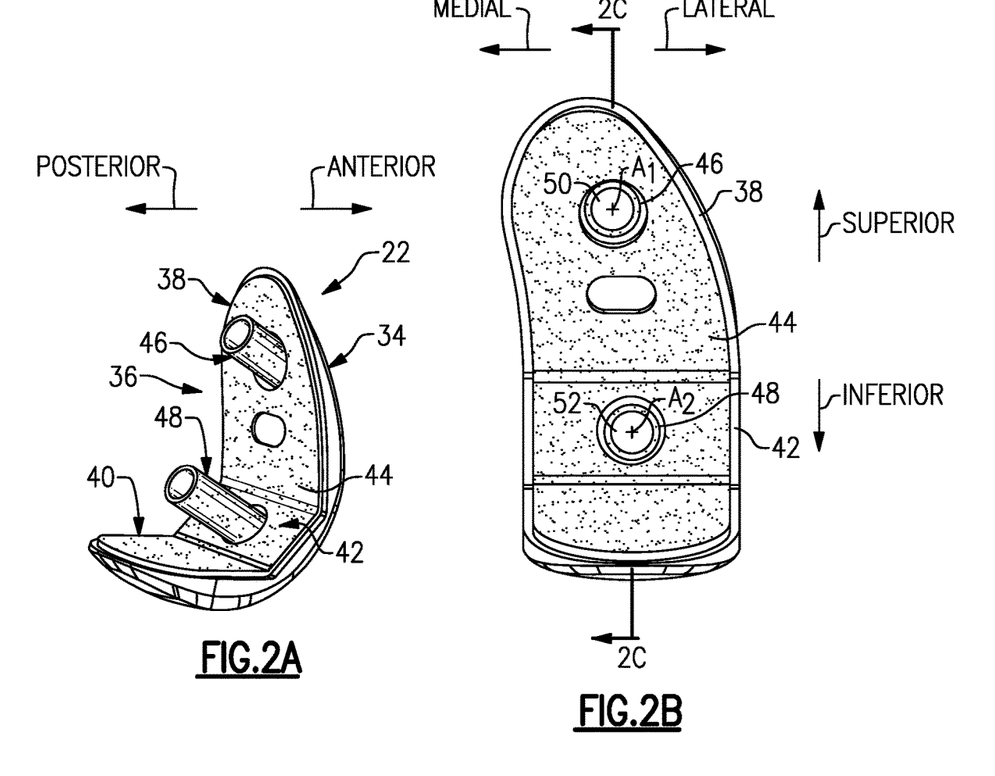
FIG. 2A is a posterior-perspective view of an example artificial femoral component.
FIG. 2B is a posterior view of the artificial femoral component of FIG. 2A.

FIG. 2A illustrates an example artificial femoral component 22 from a posterior perspective. The "anterior" and "posterior" directions are labeled across the figures for purposes of explanation only. In this example, the posterior surface 36 of the artificial component 22 has proximal and distal planar surfaces 38, 40, and a planar chamfer surface 42 extending between the proximal and distal planar surfaces 38, 40. The planar surfaces 38, 40, 42 correspond to cuts made in the femur 24.

In this example, the posterior surface 36 is substantially covered with a layer 44 of bone ingrowth material. The bone ingrowth material is relatively porous, which allows bone to grow into the layer 44. The bone ingrowth material may be provided by a metal foam material in some examples. As bone grows into the layer 44, the artificial femoral component 22 becomes biologically fixed to the femur 24. The layer 44 of bone ingrowth material may be fused to the posterior side of the femoral component 22. In another non-limiting example, the layer 44 is provided using a deposition coating process.

To further increase stability, the artificial femoral component 22 includes first and second hollow tubes 46, 48 projecting from the posterior surface 36 in a posterior direction. In this example, the first hollow tube 46 projects from the surface 38, and the second hollow tube 48 projects from the surface 42. Further, the first and second hollow tubes 46, 48 are substantially cylindrical and have a hollow interior providing respective cavities 50, 52 therein. While two hollow tubes are illustrated in this example, this disclosure extends to artificial femoral components having one or more hollow tubes.

Figure 2C:
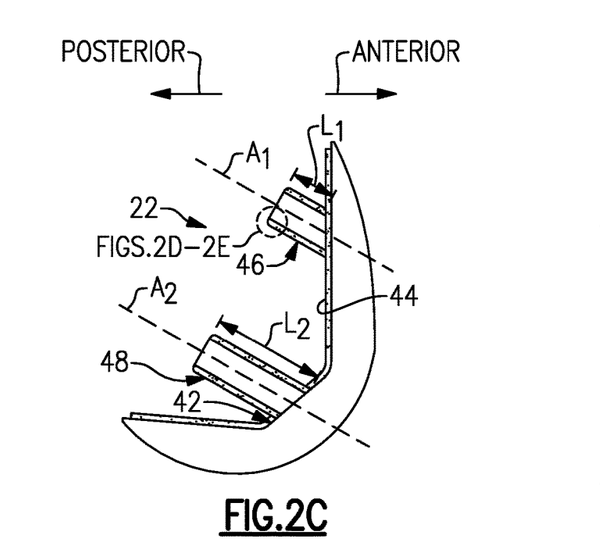
FIG. 2C is a cross-sectional view of the artificial femoral component taken along line 2C-2C of FIG. 2B.

With reference to FIG. 2B, the first hollow tube 46 is arranged about a first axis $A_1$, and the second hollow tube 48 is arranged around about a second axis $A_2$. In this example, the axes $A_1$, $A_2$ are spaced-apart from one another in the medial and lateral directions. The "medial" and "lateral" directions are shown in FIG. 2B for purposes of explanation only. Further, as seen in FIG. 2C, the first and second axes $A_1$, $A_2$ are inclined such that they are substantially parallel to one another. Additionally, in this example, the first hollow tube 46 has a length $L_1$, which is shorter than a length $L_2$ of the second hollow tube 48.

The first and second hollow tubes 46, 48 are configured such that bone may grow into the first and second cavities 50, 52, which increases the surface area of the tubes 46, 48 exposed to bone, which in turn increases fixation. But further, bone may grow into at least a portion of the first and second hollow tubes 46, 48 themselves.

Figure 2D:
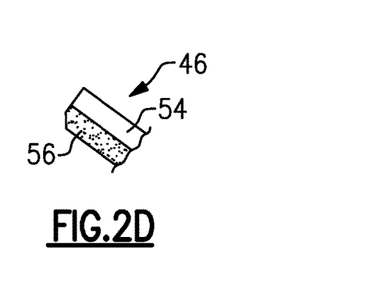
FIG. 2D is a close-up view of the encircled area in FIG. 2C, and illustrates a hollow tube with bone ingrowth material on a solid backing.
Figure 2E:
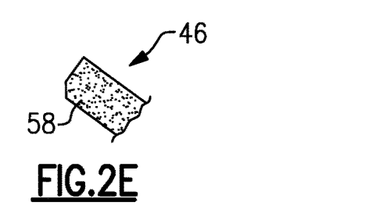
FIG. 2E is a close-up view of the encircled area of FIG. 2C, and illustrates a hollow tube made entirely of bone ingrowth material.

In one example, as illustrated in FIG. 2D, the first hollow tube 46 is provided by a solid backing material 54 supporting an outer layer 56 of bone ingrowth material. Alternatively, as illustrated in FIG. 2E, the hollow tube 46 may be provided entirely by bone ingrowth material 58. These arrangements allow bone to grow into the hollow tubes 46, 48, which increases stability and reliability of the artificial femoral component 22. While the first hollow tube 46 is illustrated in FIGS. 2D-2E, it should be understood that the second hollow tube 48 could be arranged similarly.

Figure 3A:
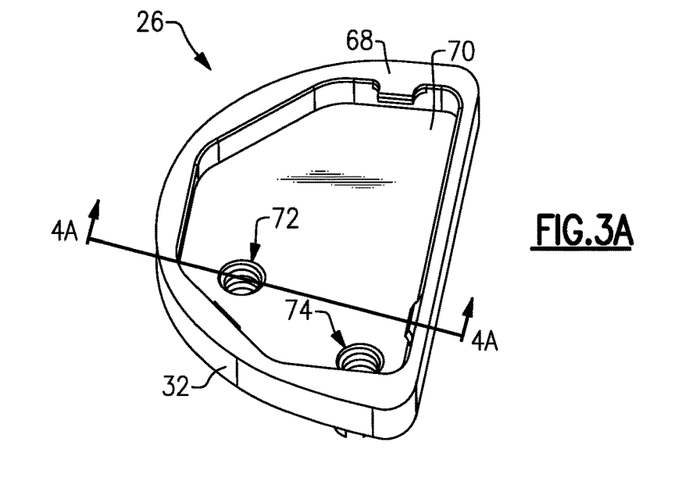
FIG. 3A is a superior-perspective view of an example artificial tibial component.
Figure 3B:
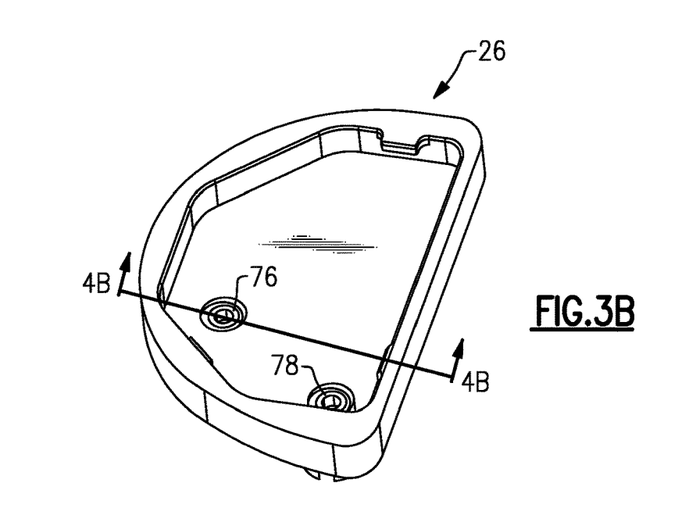
FIG. 3B is a superior-perspective view of the artificial tibial component of FIG. 3A, and illustrates first and second plugs inserted into respective openings.
Figure 3C:
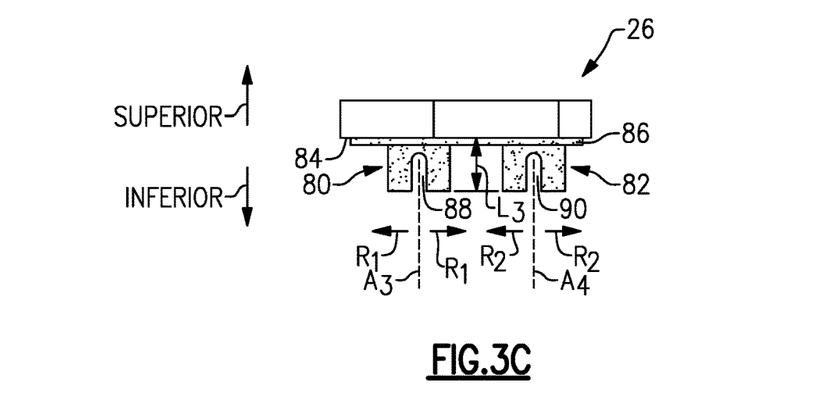
FIG. 3C is a side view of the artificial tibial component of FIG. 3A.

FIGS. 3A-3C illustrate an example artificial tibial component 26 from a superior-perspective view. In this example, the base plate 32 of the tibial component 26 includes a rim 68 extending around a perimeter and establishing a pocket 70 therein. The pocket 70 receives a portion of the spacer 30. In this example, the pocket 70 includes first and second threaded openings 72, 74. The first and second threaded openings 72, 74 are configured to receive first and second threaded plugs 76, 78, which are configured to expand respective first and second hollow tubes 80, 82 (FIG. 3C) aligned with the first and second threaded openings 72, 74, as will be discussed below. While reference is made to "threaded" openings and plugs, this disclosure extends to non-threaded arrangements. Further, while two sets of openings, plugs, and tubes are illustrated, this disclosure extends to artificial tibial components with one or more of such sets. Additionally, while the artificial tibial component 26 is shown having expandable hollow tubes, the artificial femoral component 22 could also include expandable hollow tubes. While the hollow tube may be expandable in an embodiment, in another embodiment the hollow tubes are not expandable.

In this example, an inferior surface 84 of the tibial component 26 is substantially covered by a layer 86 of bone ingrowth material. The bone ingrowth material may be the same type of bone ingrowth material as described above relative to the artificial femoral component 22, and may be applied in the same way. Further, the first and second hollow tubes 80, 82 are also provided with bone ingrowth material on a solid backing, or are alternatively provided entirely by bone ingrowth material, as in the examples of FIGS. 2D and 2E, respectively.

In this example, the first and second hollow tubes 80, 82 are provided along first and second axes $A_3$, $A_4$. The first and second axes $A_3$, $A_4$ are substantially perpendicular to the inferior surface 84 of the tibial component 26. The first and second hollow tubes 80, 82 project in the inferior direction from the inferior surface 84 by a length $L_3$.

The first and second hollow tubes 80, 82 in this example are provided with one or more slits 88, 90 along substantially the entire length $L_3$ of the first and second hollow tubes 80, 82. The slits 88, 90 allow expansion of the first and second hollow tubes 80, 82 in the radially outward directions $R_1$, $R_2$ relative to the respective axes $A_3$, $A_4$.

In one example, the first and second hollow tubes 80, 82 are selectively expandable in the radially outward directions $R_1$, $R_2$ upon insertion of the first and second plugs 76, 78 into the first and second threaded openings 72, 74. Expansion of the first and second hollow tubes 80, 82 in the radially outward directions $R_1$, $R_2$ increases the friction between the first and second hollow tubes 80, 82 and the corresponding tibial bone, which increases stability of the artificial tibial component 26.

Figure 4A:
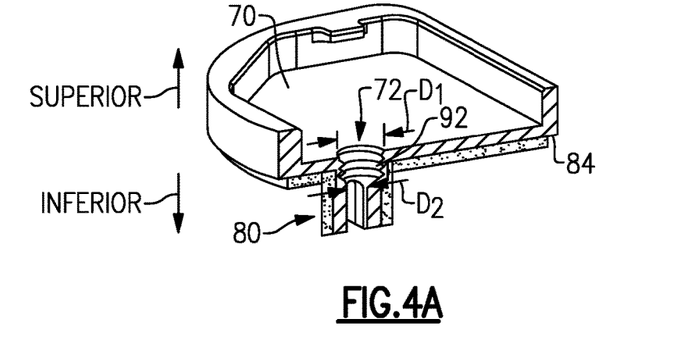
FIG. 4A is a cross-sectional view of the artificial tibial component taken along line 4A-4A of FIG. 3A.

FIG. 4A is a cross-sectional view taken along line 4A-4A from FIG. 3A. FIG. 4A illustrates the detail of the first threaded opening 72 and the first hollow tube 80. In this example, the first threaded opening 72 includes a threaded portion 92 having a first diameter $D_1$ adjacent the pocket 70. The diameter of the first threaded opening 72 gradually tapers down to a second diameter $D_2$, which is less than the first diameter $D_1$. The threaded portion 92 terminates at a point inferior to (i.e., beneath) the inferior surface 84 and within the interior of the first hollow tube 80, in this example.

Figure 5:
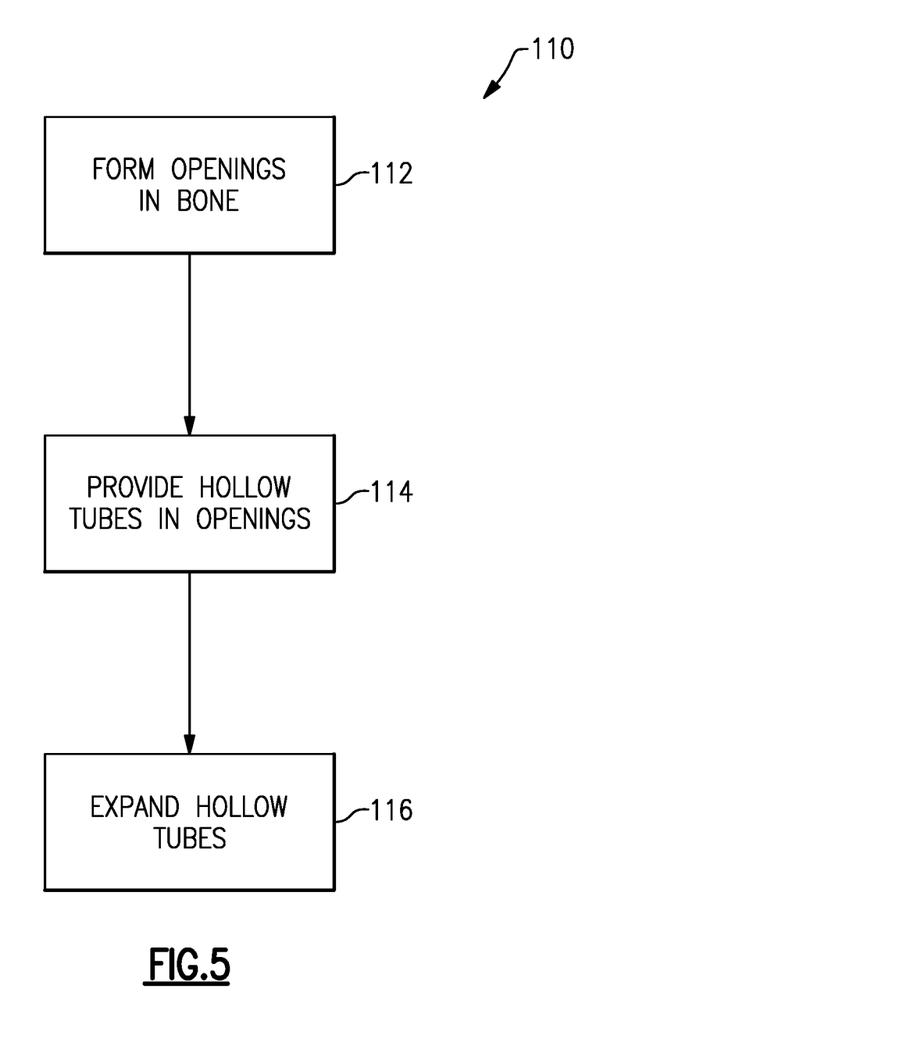
FIG. 5 is a flow chart representative of an example method according to this disclosure.

With reference to FIG. 5, an example method 110 of installing the artificial tibial component 22 is described. In the method 110, openings are formed in a bone, such as a tibial bone, at 112. Next, the first and second hollow tubes 80, 82 are received in those openings, at 114. Finally, the first and second hollow tubes 80, 82, are expanded, at 116. In one example, the first and second hollow tubes 80, 82 are expanded as the first and second threaded plugs 76, 78 are inserted into openings 72, 74.

Figures 4B, 4C, 4D:
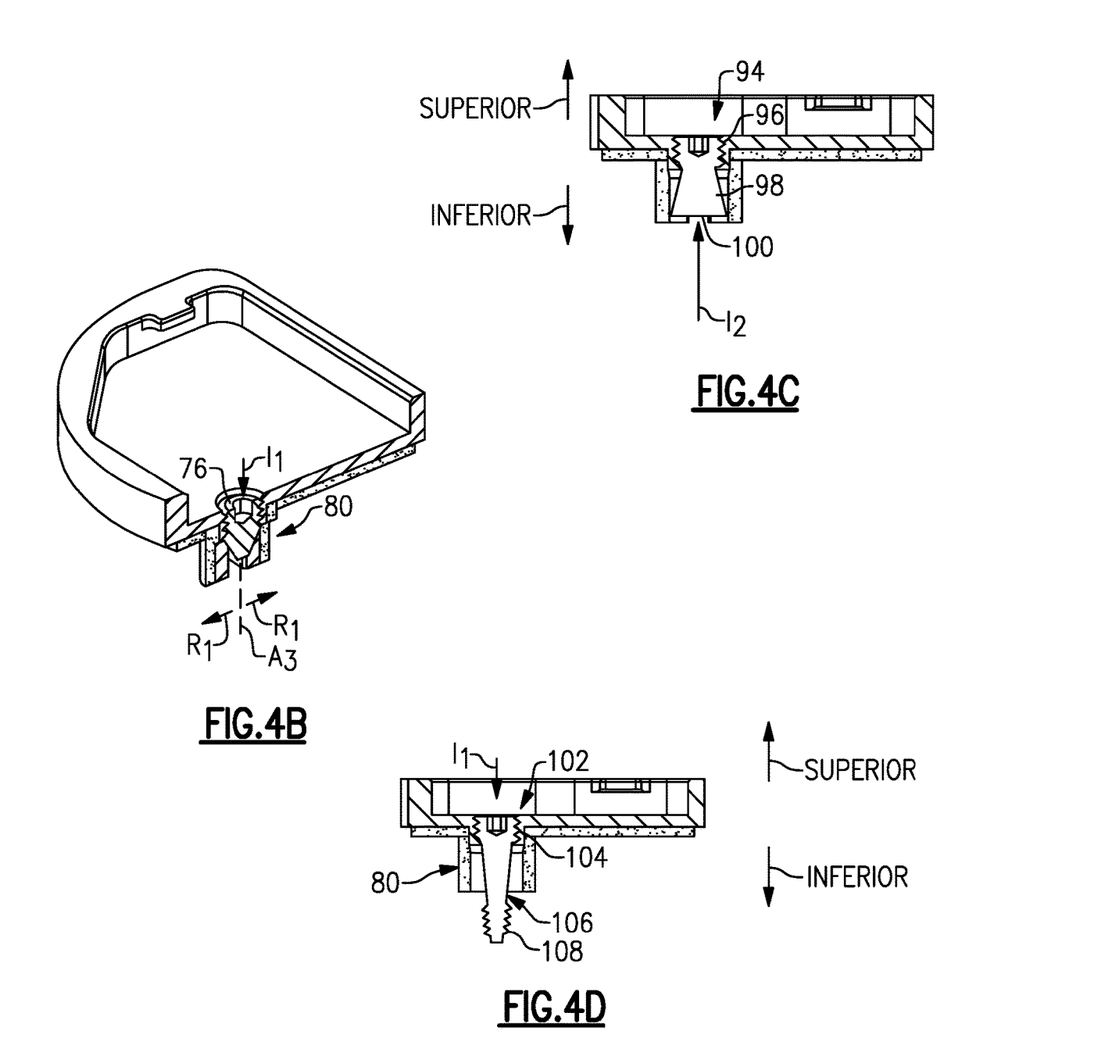
FIG. 4B is a cross-sectional view of the artificial tibial component taken along line 4B-4B of FIG. 3B.
FIG. 4C is a cross-sectional, side view of the artificial tibial component illustrating a second example plug type.
FIG. 4D is a cross-sectional, side view of the artificial tibial component illustrating a third example plug type.

Specifically, with reference to FIG. 4B, the first threaded plug 76 is inserted into the first threaded opening 72 by way of a driver, for example. In this example, the first threaded plug 76 is inserted in a first insertion direction $I_1$, from the superior side of the artificial tibial component 22 toward the inferior side of the artificial tibial component 22. The first threaded plug 76 is sized such that its outer diameter substantially corresponds to the first diameter $D_1$. As the first threaded plug 76 moves toward the second diameter $D_2$ of the first threaded opening 72, the first threaded plug 76 expands the first hollow tube 80 in the radially outward direction $R_1$ relative to the first axis $A_3$.

FIGS. 4C and 4D illustrate alternative plug configurations. FIG. 4C illustrates a second type of plug 94 having a threaded portion 96 similar to the first plug 76. Distal of the threaded portion 96, the plug 94 includes a flared portion 98. The flared portion 98 tapers from a maximum dimension at the distal end 100 of the plug 94 to the threaded portion 96. In this example, the plug 94 may be inserted in a second direction $I_2$ opposite direction $I_1$. The flared portion 98 is sized to abut the interior of the first hollow tube 80 and expand the first hollow tube 80 in the radially outward direction $R_1$.

With reference to FIG. 4D, a third type of plug 102 includes a first threaded portion 104 sized similarly to the threads of the first threaded plug 76. The plug 102 further includes a shank portion 106 configured to project beyond the inferior end of the first hollow tube 80 and including a second threaded portion 108 for engaging bone. The shank portion 106 has an outer dimension smaller than the first threaded portion 104. The first threaded portion 104 serves to expand the first hollow tube 80 in substantially the same way as the plug 76, while the second threaded portion 108 provides additional fixation relative to the tibial bone.

It should be understood that terms such as "superior," "inferior," "anterior," "posterior," "medial," "lateral," etc., are used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. An artificial femoral component configured for use in a knee arthroplasty procedure, comprising:
   a hollow tube including bone ingrowth material, wherein the hollow tube projects from a posterior surface of the artificial femoral component in a posterior direction; and
   an anterior surface configured to provide an articulating surface of an artificial knee joint, wherein the anterior surface is on an opposite side of the artificial femoral component as the posterior surface.

2. The artificial femoral component as recited in claim 1, wherein the posterior surface is substantially covered with a layer of bone ingrowth material.

3. The artificial femoral component as recited in claim 1, wherein:
   the posterior surface includes a proximal planar surface, a distal planar surface, and a planar chamfer surface between the proximal planar surface and the distal planar surface, and
   the hollow tube projects from one of the proximal planar surface and the planar chamfer surface.

4. The artificial femoral component as recited in claim 1, wherein the hollow tube is provided by solid backing material and an outer layer of the bone ingrowth material.

5. The artificial femoral component as recited in claim 1, wherein the hollow tube consists of bone ingrowth material.

6. The artificial femoral component as recited in claim 1, wherein the bone ingrowth material is porous.

7. The artificial femoral component as recited in claim 1, wherein the bone ingrowth material comprises a metal foam.

8. An artificial femoral component configured for use in a knee arthroplasty procedure, comprising:
   a hollow tube including bone ingrowth material, wherein the hollow tube projects from a posterior surface of the artificial femoral component in a posterior direction,
   wherein the posterior surface includes a proximal planar surface, a distal planar surface, and a planar chamfer surface between the proximal planar surface and the distal planar surface,
   wherein the hollow tube projects from one of the proximal planar surface and the planar chamfer surface,
   wherein the hollow tube is a first hollow tube and the artificial femoral component further comprises a second hollow tube,
   wherein the first hollow tube projects from the proximal planar surface, and
   wherein the second hollow tube projects from the planar chamfer surface.

9. The artificial femoral component as recited in claim 8, wherein:
   the first hollow tube is arranged about a first axis, and
   the second hollow tube is arranged about a second axis spaced-apart from the first axis.

10. The artificial femoral component as recited in claim 9, wherein the first and second axes are substantially parallel to one another.

11. The artificial femoral component as recited in claim 9, wherein the first and second axes are spaced-apart from one another in a direction normal to the posterior direction.

12. The artificial femoral component as recited in claim 8, wherein:
   the first hollow tube projects from the proximal planar surface by a first length, and
   the second hollow tube projects from the planar chamfer surface by a second length different than the first length.

13. The artificial femoral component as recited in claim 12, first length is shorter than the second length.

14. An artificial joint component configured for use in an arthroplasty procedure, comprising:
   a hollow tube including bone ingrowth material, wherein the hollow tube is selectively expandable; and
   an anterior surface configured to provide an articulating surface of an artificial joint, wherein the hollow tube is arranged on an opposite side of the artificial component as the articulating surface.

\* \* \* \* \*